US009504821B2

(12) United States Patent
Ameri et al.

(10) Patent No.: US 9,504,821 B2
(45) Date of Patent: Nov. 29, 2016

(54) CONSTRUCTION OF AN MRI-SAFE TACHYCARDIA LEAD

(71) Applicant: Cardiac Pacemakers, Inc., St. Paul, MN (US)

(72) Inventors: Masoud Ameri, Maple Plain, MN (US); G. Shantanu Reddy, Minneapolis, MN (US); Joseph Walker, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 14/631,010

(22) Filed: Feb. 25, 2015

(65) Prior Publication Data

US 2015/0238756 A1 Aug. 27, 2015

Related U.S. Application Data

(60) Provisional application No. 61/945,081, filed on Feb. 26, 2014.

(51) Int. Cl.
*A61N 1/08* (2006.01)
*A61N 1/05* (2006.01)
*H01R 43/00* (2006.01)

(52) U.S. Cl.
CPC .............. *A61N 1/08* (2013.01); *A61N 1/0558* (2013.01); *A61N 1/0563* (2013.01); *H01R 43/00* (2013.01); *A61N 2001/086* (2013.01); *Y10T 29/49002* (2015.01); *Y10T 29/49117* (2015.01)

(58) Field of Classification Search
CPC .... A61N 1/08; A61N 1/0563; A61N 1/0558; A61N 2001/086; H01R 43/00; Y10T 29/49117; Y10T 29/49002
See application file for complete search history.

(56) References Cited

U.S. PATENT DOCUMENTS

| 3,614,692 A | 10/1971 | Rozelle et al. |
| 4,131,759 A | 12/1978 | Felkel |

(Continued)

FOREIGN PATENT DOCUMENTS

| CN | 1762510 A | 4/2006 |
| CN | 1905789 A | 1/2007 |

(Continued)

OTHER PUBLICATIONS

International Search Report and Written Opinion issued in PCT/US2013/065517, mailed Dec. 20, 2013, 11 pgs.

(Continued)

*Primary Examiner* — Rex R Holmes
(74) *Attorney, Agent, or Firm* — Faegre Baker Daniels LLP

(57) ABSTRACT

A medical device lead includes a tubular conductive element disposed over a lead body. The tubular conductive element includes at least one segment having one or more kerfs formed radially therethrough in a predetermined configuration so as to affect at least one electrical property, e.g., electrical impedance, of the segment. The segment may form a shocking conductor of the medical device lead. The tubular conductive element may alternatively include proximal, intermediate and distal segments each having one or more kerfs formed radially therethrough, where the one or more kerfs in each of the proximal and intermediate segments are configured so that these segments each have a higher electrical impedance than the distal segment. A layer of insulative material is disposed over the proximal and intermediate segments, so that the proximal and intermediate segments of the tubular conductive element are operable to filter electromagnetic energy from an external source.

16 Claims, 6 Drawing Sheets

(56) References Cited

U.S. PATENT DOCUMENTS

| | | |
|---|---|---|
| 4,135,518 A | 1/1979 | Dutcher |
| 4,146,036 A | 3/1979 | Dutcher et al. |
| 4,209,019 A | 6/1980 | Dutcher et al. |
| 4,253,462 A | 3/1981 | Dutcher et al. |
| 4,350,169 A | 9/1982 | Dutcher et al. |
| 4,381,013 A | 4/1983 | Dutcher |
| 4,404,125 A | 9/1983 | Abolins et al. |
| 4,437,474 A | 3/1984 | Peers-Trevarton |
| 4,484,586 A | 11/1984 | McMickle et al. |
| 4,493,329 A | 1/1985 | Crawford et al. |
| 4,574,800 A | 3/1986 | Peers-Trevarton |
| 4,643,202 A | 2/1987 | Roche |
| 4,643,203 A | 2/1987 | Labbe |
| 4,649,938 A | 3/1987 | McArthur |
| 4,869,970 A | 9/1989 | Gulla et al. |
| 5,002,067 A | 3/1991 | Berthelsen et al. |
| 5,003,975 A | 4/1991 | Hafelfinger et al. |
| 5,020,545 A | 6/1991 | Soukup |
| 5,056,516 A | 10/1991 | Spehr |
| 5,074,313 A | 12/1991 | Dahl et al. |
| 5,144,960 A | 9/1992 | Mehra et al. |
| 5,201,865 A | 4/1993 | Kuehn |
| 5,217,010 A | 6/1993 | Tsitlik et al. |
| 5,222,506 A | 6/1993 | Patrick et al. |
| 5,231,996 A | 8/1993 | Bardy et al. |
| 5,241,957 A | 9/1993 | Camps et al. |
| 5,243,911 A | 9/1993 | Dow et al. |
| 5,246,014 A | 9/1993 | Williams et al. |
| 5,259,395 A | 11/1993 | Li |
| 5,300,108 A | 4/1994 | Rebell et al. |
| 5,324,322 A | 6/1994 | Grill, Jr. et al. |
| 5,330,522 A | 7/1994 | Kreyenhagen |
| 5,354,327 A | 10/1994 | Smits |
| 5,370,666 A | 12/1994 | Lindberg et al. |
| 5,378,234 A | 1/1995 | Hammerslag et al. |
| 5,387,199 A | 2/1995 | Siman et al. |
| 5,417,208 A | 5/1995 | Winkler |
| 5,425,755 A | 6/1995 | Doan |
| 5,456,707 A | 10/1995 | Giele |
| 5,476,485 A | 12/1995 | Weinberg et al. |
| 5,483,022 A | 1/1996 | Mar |
| 5,522,872 A | 6/1996 | Hoff |
| 5,522,875 A | 6/1996 | Gates et al. |
| 5,534,018 A | 7/1996 | Wahlstrand et al. |
| 5,542,173 A | 8/1996 | Mar et al. |
| 5,542,174 A | 8/1996 | Chiu |
| 5,545,205 A | 8/1996 | Schulte et al. |
| 5,549,646 A | 8/1996 | Katz et al. |
| 5,554,139 A | 9/1996 | Okajima |
| 5,574,249 A | 11/1996 | Lindsay |
| 5,584,873 A | 12/1996 | Shoberg et al. |
| 5,599,576 A | 2/1997 | Opolski |
| 5,609,622 A | 3/1997 | Soukup et al. |
| 5,618,208 A | 4/1997 | Crouse et al. |
| 5,649,974 A | 7/1997 | Nelson et al. |
| 5,658,709 A | 8/1997 | Layman et al. |
| 5,676,694 A | 10/1997 | Boser et al. |
| 5,727,552 A | 3/1998 | Ryan |
| 5,727,553 A | 3/1998 | Saad |
| 5,728,149 A | 3/1998 | Laske et al. |
| 5,755,742 A | 5/1998 | Schuelke et al. |
| 5,760,341 A | 6/1998 | Laske et al. |
| 5,766,227 A | 6/1998 | Nappholz et al. |
| 5,800,496 A | 9/1998 | Swoyer et al. |
| 5,810,887 A | 9/1998 | Accorti, Jr. et al. |
| 5,817,136 A | 10/1998 | Nappholz et al. |
| 5,824,026 A | 10/1998 | Diaz |
| 5,833,715 A | 11/1998 | Vachon et al. |
| 5,849,031 A | 12/1998 | Martinez et al. |
| 5,891,114 A | 4/1999 | Chien et al. |
| 5,891,179 A | 4/1999 | Er et al. |
| 5,935,159 A | 8/1999 | Cross, Jr. et al. |
| 5,957,966 A | 9/1999 | Schroeppel et al. |
| 5,957,970 A | 9/1999 | Shoberg et al. |
| 5,968,087 A | 10/1999 | Hess et al. |
| 6,016,447 A | 1/2000 | Juran et al. |
| 6,057,031 A | 5/2000 | Breme et al. |
| 6,078,840 A | 6/2000 | Stokes |
| 6,083,216 A | 7/2000 | Fischer, Sr. |
| 6,101,417 A | 8/2000 | Vogel et al. |
| 6,106,522 A | 8/2000 | Fleischman et al. |
| 6,141,593 A | 10/2000 | Patag |
| 6,143,013 A | 11/2000 | Samson et al. |
| 6,178,355 B1 | 1/2001 | Williams et al. |
| 6,192,280 B1 | 2/2001 | Sommer et al. |
| 6,208,881 B1 | 3/2001 | Champeau |
| 6,249,708 B1 | 6/2001 | Nelson et al. |
| 6,256,541 B1 | 7/2001 | Heil et al. |
| 6,259,954 B1 | 7/2001 | Conger et al. |
| 6,289,250 B1 | 9/2001 | Tsuboi et al. |
| 6,295,476 B1 | 9/2001 | Schaenzer |
| 6,304,784 B1 | 10/2001 | Allee et al. |
| 6,317,633 B1 | 11/2001 | Jorgenson et al. |
| 6,360,129 B1 | 3/2002 | Ley et al. |
| 6,400,992 B1 | 6/2002 | Borgersen et al. |
| 6,428,537 B1 | 8/2002 | Swanson et al. |
| 6,434,430 B2 | 8/2002 | Borgersen et al. |
| 6,456,888 B1 | 9/2002 | Skinner et al. |
| 6,493,591 B1 | 12/2002 | Stokes |
| 6,501,991 B1 | 12/2002 | Honeck et al. |
| 6,501,994 B1 | 12/2002 | Janke et al. |
| 6,510,345 B1 | 1/2003 | Van Bentem |
| 6,516,230 B2 | 2/2003 | Williams et al. |
| 6,526,321 B1 | 2/2003 | Spehr |
| 6,564,107 B1 | 5/2003 | Bodner et al. |
| 6,671,554 B2 | 12/2003 | Gibson et al. |
| 6,701,191 B2 | 3/2004 | Schell |
| 6,721,600 B2 | 4/2004 | Jorgenson et al. |
| 6,721,604 B1 | 4/2004 | Robinson et al. |
| 6,813,251 B1 | 11/2004 | Garney et al. |
| 6,813,521 B2 | 11/2004 | Bischoff et al. |
| 6,850,803 B1 | 2/2005 | Jimenez et al. |
| 6,854,994 B2 | 2/2005 | Stein et al. |
| 6,866,044 B2 | 3/2005 | Bardy et al. |
| 6,906,256 B1 | 6/2005 | Wang |
| 6,909,256 B2 | 6/2005 | Itabashi |
| 6,920,361 B2 | 7/2005 | Williams |
| 6,925,334 B1 | 8/2005 | Salys |
| 6,944,489 B2 | 9/2005 | Zeijlemaker et al. |
| 6,949,929 B2 | 9/2005 | Gray et al. |
| 6,978,185 B2 | 12/2005 | Osypka |
| 6,985,755 B2 | 1/2006 | Cadieux et al. |
| 6,985,775 B2 | 1/2006 | Rinke et al. |
| 6,993,373 B2 | 1/2006 | Vrijheid et al. |
| 6,999,818 B2 | 2/2006 | Stevenson et al. |
| 6,999,821 B2 | 2/2006 | Jenney et al. |
| 7,013,180 B2 | 3/2006 | Dublin et al. |
| 7,013,182 B1 | 3/2006 | Krishnan |
| 7,047,075 B2 | 5/2006 | Stubbs |
| 7,047,083 B2 | 5/2006 | Gunderson et al. |
| 7,050,855 B2 | 5/2006 | Zeijlemaker et al. |
| 7,113,827 B2 | 9/2006 | Silvestri et al. |
| 7,123,013 B2 | 10/2006 | Gray |
| 7,127,294 B1 | 10/2006 | Wang et al. |
| 7,135,978 B2 | 11/2006 | Gisselberg et al. |
| 7,138,582 B2 | 11/2006 | Lessar et al. |
| 7,158,837 B2 | 1/2007 | Osypka et al. |
| 7,174,219 B2 | 2/2007 | Wahlstrand et al. |
| 7,174,220 B1 | 2/2007 | Chitre et al. |
| 7,205,768 B2 | 4/2007 | Schulz et al. |
| 7,239,916 B2 | 7/2007 | Thompson et al. |
| 7,242,987 B2 | 7/2007 | Holleman et al. |
| 7,257,449 B2 | 8/2007 | Bodner |
| 7,289,851 B2 | 10/2007 | Gunderson et al. |
| 7,363,090 B2 | 4/2008 | Halperin et al. |
| 7,369,898 B1 | 5/2008 | Kroll et al. |
| 7,378,931 B2 | 5/2008 | Odahara et al. |
| 7,388,378 B2 | 6/2008 | Gray et al. |
| 7,389,148 B1 | 6/2008 | Morgan |
| 7,453,344 B2 | 11/2008 | Maeda et al. |
| 7,535,363 B2 | 5/2009 | Gisselberg et al. |
| 7,571,010 B2 | 8/2009 | Zarembo et al. |
| 7,584,005 B1 | 9/2009 | Jain |
| 7,610,101 B2 | 10/2009 | Wedan et al. |

(56) References Cited

U.S. PATENT DOCUMENTS

| | | |
|---|---|---|
| 7,630,761 B2 | 12/2009 | Salo et al. |
| 7,689,291 B2 | 3/2010 | Polkinghorne et al. |
| 7,765,005 B2 | 7/2010 | Stevenson |
| 7,853,332 B2 | 12/2010 | Olsen et al. |
| 7,877,150 B2 | 1/2011 | Hoegh et al. |
| 7,912,552 B2 | 3/2011 | Przybyszewski |
| 7,917,213 B2 | 3/2011 | Bulkes et al. |
| 7,933,662 B2 | 4/2011 | Marshall et al. |
| 7,953,499 B2 | 5/2011 | Knapp et al. |
| 7,986,999 B2 | 7/2011 | Wedan et al. |
| 7,991,484 B1 | 8/2011 | Sengupta et al. |
| 8,000,801 B2 | 8/2011 | Stevenson et al. |
| 8,027,736 B2 | 9/2011 | Wahlstrand et al. |
| 8,032,230 B1 | 10/2011 | Cox et al. |
| 8,046,084 B2 | 10/2011 | Bodner |
| 8,099,177 B2 | 1/2012 | Dahlberg |
| 8,103,360 B2 | 1/2012 | Foster |
| 8,108,054 B2 | 1/2012 | Helland |
| 8,145,324 B1 | 3/2012 | Stevenson et al. |
| 8,170,688 B2 | 5/2012 | Wedan et al. |
| 8,200,342 B2 | 6/2012 | Stevenson et al. |
| 8,214,055 B2 | 7/2012 | Erickson |
| 8,244,346 B2 | 8/2012 | Foster et al. |
| 8,255,055 B2 | 8/2012 | Ameri |
| 8,306,630 B2 | 11/2012 | Stubbs et al. |
| 8,315,715 B2 | 11/2012 | Erickson |
| 8,332,050 B2 | 12/2012 | Perrey et al. |
| 8,335,572 B2 | 12/2012 | Ameri |
| 8,369,964 B2 | 2/2013 | Ameri |
| 8,391,994 B2 | 3/2013 | Foster et al. |
| 8,401,671 B2 | 3/2013 | Wedan et al. |
| 8,406,895 B2 | 3/2013 | Erbstoeszer et al. |
| 8,543,209 B2 | 9/2013 | Tyers et al. |
| 8,543,218 B2 | 9/2013 | Erickson |
| 8,666,508 B2 | 3/2014 | Foster et al. |
| 8,666,512 B2 | 3/2014 | Walker et al. |
| 8,670,828 B2 | 3/2014 | Hall et al. |
| 8,670,840 B2 | 3/2014 | Wedan et al. |
| 8,676,344 B2 | 3/2014 | Desai et al. |
| 8,676,351 B2 | 3/2014 | Foster et al. |
| 8,682,451 B2 | 3/2014 | Wengreen et al. |
| 8,688,236 B2 | 4/2014 | Foster |
| 8,731,685 B2 | 5/2014 | Ameri |
| 8,744,600 B2 | 6/2014 | Perrey et al. |
| 8,798,767 B2 | 8/2014 | Foster et al. |
| 8,825,179 B2 | 9/2014 | Walker et al. |
| 8,825,181 B2 | 9/2014 | Foster et al. |
| 8,954,168 B2 | 2/2015 | Foster |
| 8,983,623 B2 | 3/2015 | Foster et al. |
| 9,050,457 B2 | 6/2015 | Foster et al. |
| 9,199,077 B2 | 12/2015 | Foster et al. |
| 9,203,648 B2 | 12/2015 | Shraim et al. |
| 9,254,380 B2 | 2/2016 | Ameri et al. |
| 2002/0065544 A1 | 5/2002 | Smits |
| 2002/0072769 A1 | 6/2002 | Silvian et al. |
| 2002/0111664 A1 | 8/2002 | Bartig et al. |
| 2002/0128689 A1 | 9/2002 | Connelly et al. |
| 2002/0144720 A1 | 10/2002 | Zahorik et al. |
| 2003/0028231 A1 | 2/2003 | Partridge et al. |
| 2003/0050680 A1 | 3/2003 | Gibson et al. |
| 2003/0063946 A1 | 4/2003 | Williams et al. |
| 2003/0083723 A1 | 5/2003 | Wilkinson et al. |
| 2003/0083726 A1 | 5/2003 | Zeijlemaker et al. |
| 2003/0092303 A1 | 5/2003 | Osypka |
| 2003/0093136 A1 | 5/2003 | Osypka et al. |
| 2003/0093138 A1 | 5/2003 | Osypka et al. |
| 2003/0139794 A1 | 7/2003 | Jenney et al. |
| 2003/0140931 A1 | 7/2003 | Zeijlemaker et al. |
| 2003/0144705 A1 | 7/2003 | Funke |
| 2003/0144716 A1 | 7/2003 | Reinke et al. |
| 2003/0144718 A1 | 7/2003 | Zeijlemaker |
| 2003/0144719 A1 | 7/2003 | Zeijlemaker |
| 2003/0144720 A1 | 7/2003 | Villaseca et al. |
| 2003/0144721 A1 | 7/2003 | Villaseca et al. |
| 2003/0204217 A1 | 10/2003 | Greatbatch |
| 2004/0014355 A1 | 1/2004 | Osypka et al. |
| 2004/0064161 A1 | 4/2004 | Gunderson et al. |
| 2004/0064173 A1 | 4/2004 | Hine et al. |
| 2004/0064174 A1 | 4/2004 | Belden |
| 2004/0088033 A1 | 5/2004 | Smits et al. |
| 2004/0097965 A1 | 5/2004 | Gardeski et al. |
| 2004/0122490 A1 | 6/2004 | Reinke et al. |
| 2004/0153049 A1 | 8/2004 | Hewitt et al. |
| 2004/0162600 A1 | 8/2004 | Williams |
| 2004/0167442 A1 | 8/2004 | Shireman et al. |
| 2004/0172117 A1 | 9/2004 | Hill et al. |
| 2004/0193140 A1 | 9/2004 | Griffin et al. |
| 2004/0243210 A1 | 12/2004 | Morgan et al. |
| 2004/0267107 A1 | 12/2004 | Lessar et al. |
| 2005/0030322 A1 | 2/2005 | Gardos |
| 2005/0070972 A1 | 3/2005 | Wahlstrand et al. |
| 2005/0090886 A1 | 4/2005 | MacDonald et al. |
| 2005/0113676 A1 | 5/2005 | Weiner et al. |
| 2005/0113873 A1 | 5/2005 | Weiner et al. |
| 2005/0113876 A1 | 5/2005 | Weiner et al. |
| 2005/0136385 A1 | 6/2005 | Mann et al. |
| 2005/0177135 A1 | 8/2005 | Hildebrand et al. |
| 2005/0182471 A1 | 8/2005 | Wang |
| 2005/0197677 A1 | 9/2005 | Stevenson |
| 2005/0222642 A1 | 10/2005 | Przybyszewski et al. |
| 2005/0222656 A1 | 10/2005 | Wahlstrand et al. |
| 2005/0222657 A1 | 10/2005 | Wahlstrand et al. |
| 2005/0222658 A1 | 10/2005 | Hoegh et al. |
| 2005/0222659 A1 | 10/2005 | Olsen et al. |
| 2005/0227398 A1 | 10/2005 | Anderson et al. |
| 2005/0246007 A1 | 11/2005 | Sommer et al. |
| 2005/0267556 A1 | 12/2005 | Shuros et al. |
| 2005/0272280 A1 | 12/2005 | Osypka |
| 2005/0283167 A1 | 12/2005 | Gray |
| 2006/0009819 A1 | 1/2006 | Przybyszewski |
| 2006/0030774 A1 | 2/2006 | Gray et al. |
| 2006/0037461 A1 | 2/2006 | Yasumura |
| 2006/0041293 A1 | 2/2006 | Mehdizadeh et al. |
| 2006/0041294 A1 | 2/2006 | Gray |
| 2006/0041296 A1 | 2/2006 | Bauer et al. |
| 2006/0089691 A1 | 4/2006 | Kaplan et al. |
| 2006/0089695 A1 | 4/2006 | Bolea et al. |
| 2006/0089696 A1 | 4/2006 | Olsen et al. |
| 2006/0093685 A1 | 5/2006 | Mower et al. |
| 2006/0105066 A1 | 5/2006 | Teague et al. |
| 2006/0106442 A1 | 5/2006 | Richardson et al. |
| 2006/0118758 A1 | 6/2006 | Wang et al. |
| 2006/0129043 A1 | 6/2006 | Ben-Jacob et al. |
| 2006/0167536 A1 | 7/2006 | Nygren et al. |
| 2006/0200218 A1 | 9/2006 | Wahlstrand |
| 2006/0229693 A1 | 10/2006 | Bauer et al. |
| 2006/0247747 A1 | 11/2006 | Olsen et al. |
| 2006/0247748 A1 | 11/2006 | Wahlstrand et al. |
| 2006/0252314 A1 | 11/2006 | Atalar et al. |
| 2006/0253180 A1 | 11/2006 | Zarembo et al. |
| 2006/0271138 A1 | 11/2006 | MacDonald |
| 2006/0293737 A1 | 12/2006 | Krishnan |
| 2007/0010702 A1 | 1/2007 | Wang et al. |
| 2007/0027532 A1 | 2/2007 | Wang et al. |
| 2007/0106332 A1 | 5/2007 | Denker et al. |
| 2007/0112398 A1 | 5/2007 | Stevenson et al. |
| 2007/0156205 A1 | 7/2007 | Larson et al. |
| 2007/0179577 A1 | 8/2007 | Marshall et al. |
| 2007/0179582 A1 | 8/2007 | Marshall et al. |
| 2007/0191914 A1 | 8/2007 | Stessman |
| 2007/0208383 A1 | 9/2007 | Williams |
| 2007/0255378 A1 | 11/2007 | Polkinghorne et al. |
| 2008/0009905 A1 | 1/2008 | Zeijlemaker |
| 2008/0033497 A1 | 2/2008 | Bulkes et al. |
| 2008/0039709 A1 | 2/2008 | Karmarkar |
| 2008/0049376 A1 | 2/2008 | Stevenson et al. |
| 2008/0051854 A1 | 2/2008 | Bulkes et al. |
| 2008/0057784 A1 | 3/2008 | Zarembo et al. |
| 2008/0058902 A1 | 3/2008 | Gray et al. |
| 2008/0119917 A1 | 5/2008 | Geistert |
| 2008/0125754 A1 | 5/2008 | Beer et al. |
| 2008/0129435 A1 | 6/2008 | Gray |
| 2008/0132985 A1 | 6/2008 | Wedan et al. |
| 2008/0132986 A1 | 6/2008 | Gray et al. |

(56) References Cited

U.S. PATENT DOCUMENTS

| | | |
|---|---|---|
| 2008/0140152 A1 | 6/2008 | Imran et al. |
| 2008/0154348 A1 | 6/2008 | Atalar et al. |
| 2008/0208290 A1 | 8/2008 | Phillips et al. |
| 2008/0243218 A1 | 10/2008 | Bottomley et al. |
| 2008/0262584 A1 | 10/2008 | Bottomley et al. |
| 2008/0269831 A1 | 10/2008 | Erickson |
| 2009/0005825 A1 | 1/2009 | MacDonald |
| 2009/0024180 A1 | 1/2009 | Kisker et al. |
| 2009/0024197 A1 | 1/2009 | Jensen |
| 2009/0099440 A1 | 4/2009 | Viohl |
| 2009/0099555 A1 | 4/2009 | Viohl et al. |
| 2009/0118610 A1 | 5/2009 | Karmarkar et al. |
| 2009/0149920 A1 | 6/2009 | Li et al. |
| 2009/0149933 A1 | 6/2009 | Ameri |
| 2009/0149934 A1 | 6/2009 | Ameri et al. |
| 2009/0198314 A1 | 8/2009 | Foster et al. |
| 2009/0204171 A1 | 8/2009 | Ameri |
| 2009/0210022 A1 | 8/2009 | Powers |
| 2009/0270948 A1 | 10/2009 | Nghiem et al. |
| 2009/0270956 A1 | 10/2009 | Vase et al. |
| 2009/0281608 A1 | 11/2009 | Foster |
| 2010/0010602 A1 | 1/2010 | Wedan et al. |
| 2010/0016935 A1 | 1/2010 | Strandberg et al. |
| 2010/0049290 A1 | 2/2010 | Min et al. |
| 2010/0103215 A1 | 4/2010 | Iriguchi |
| 2010/0106215 A1 | 4/2010 | Stubbs et al. |
| 2010/0114277 A1 | 5/2010 | Zhao et al. |
| 2010/0125320 A1 | 5/2010 | Polkinghorne et al. |
| 2010/0137928 A1 | 6/2010 | Duncan et al. |
| 2010/0174348 A1 | 7/2010 | Bulkes et al. |
| 2010/0174349 A1 | 7/2010 | Stevenson et al. |
| 2010/0234929 A1 | 9/2010 | Scheuermann |
| 2010/0249892 A1 | 9/2010 | Bulkes et al. |
| 2010/0292744 A1 | 11/2010 | Hill et al. |
| 2010/0331936 A1 | 12/2010 | Perrey et al. |
| 2011/0060394 A1 | 3/2011 | Poore |
| 2011/0079423 A1 | 4/2011 | Zhao et al. |
| 2011/0087299 A1 | 4/2011 | Ameri |
| 2011/0087302 A1 | 4/2011 | Ameri |
| 2011/0093054 A1 | 4/2011 | Ameri |
| 2011/0160805 A1 | 6/2011 | Erbstoeszer et al. |
| 2011/0160816 A1 | 6/2011 | Stubbs et al. |
| 2011/0160817 A1 | 6/2011 | Foster et al. |
| 2011/0160818 A1 | 6/2011 | Struve |
| 2011/0160828 A1 | 6/2011 | Foster et al. |
| 2011/0160829 A1 | 6/2011 | Foster et al. |
| 2011/0208280 A1 | 8/2011 | Li et al. |
| 2011/0218422 A1 | 9/2011 | Atalar et al. |
| 2011/0238146 A1 | 9/2011 | Wedan et al. |
| 2011/0288403 A1 | 11/2011 | Kondabatni et al. |
| 2012/0016451 A1 | 1/2012 | Struve et al. |
| 2012/0022356 A1 | 1/2012 | Olsen et al. |
| 2012/0035698 A1 | 2/2012 | Johnson et al. |
| 2012/0053662 A1 | 3/2012 | Foster et al. |
| 2012/0101558 A1 | 4/2012 | Kampa et al. |
| 2012/0109270 A1 | 5/2012 | Foster |
| 2012/0143273 A1 | 6/2012 | Stubbs et al. |
| 2012/0161901 A1 | 6/2012 | Stevenson et al. |
| 2012/0179233 A1 | 7/2012 | Wedan et al. |
| 2012/0232609 A1 | 9/2012 | Tyers et al. |
| 2012/0253340 A1 | 10/2012 | Stevenson et al. |
| 2012/0271394 A1 | 10/2012 | Foster et al. |
| 2013/0116764 A1 | 5/2013 | Walker et al. |
| 2013/0158641 A1 | 6/2013 | Foster et al. |
| 2013/0190849 A1 | 7/2013 | Perrey et al. |
| 2013/0190850 A1 | 7/2013 | Wedan et al. |
| 2013/0282093 A1 | 10/2013 | Walker et al. |
| 2013/0325093 A1 | 12/2013 | Foster |
| 2014/0067030 A1 | 3/2014 | Walker et al. |
| 2014/0114383 A1 | 4/2014 | Foster et al. |
| 2014/0155972 A1 | 6/2014 | Foster et al. |
| 2014/0324139 A1 | 10/2014 | Foster et al. |
| 2015/0105846 A1 | 4/2015 | Foster |
| 2015/0182744 A1 | 7/2015 | Foster et al. |

FOREIGN PATENT DOCUMENTS

| | | |
|---|---|---|
| CN | 101039619 A | 9/2007 |
| CN | 101553165 B | 10/2009 |
| CN | 102186534 A | 9/2011 |
| CN | 102209575 A | 10/2011 |
| CN | 104736196 A | 6/2015 |
| EP | 0897997 B1 | 2/2003 |
| EP | 1594564 A1 | 11/2005 |
| EP | 1852810 B1 | 11/2007 |
| EP | 2445577 B1 | 5/2012 |
| EP | 2227289 B1 | 7/2015 |
| EP | 2890446 A1 | 7/2015 |
| EP | 2908903 A1 | 8/2015 |
| JP | H0747139 A | 2/1995 |
| JP | 2001522631 A | 11/2001 |
| JP | 2004511293 A | 4/2004 |
| JP | 2004141679 A | 5/2004 |
| JP | 2005501673 A | 1/2005 |
| JP | 2005515852 A | 6/2005 |
| JP | 2005515854 A | 6/2005 |
| JP | 2005522301 A | 7/2005 |
| JP | 2007520254 A | 7/2007 |
| JP | 2011504405 A | 2/2011 |
| JP | 2011509813 A | 3/2011 |
| JP | 2015520007 A | 7/2015 |
| WO | WO9606655 A1 | 3/1996 |
| WO | WO9923958 A1 | 5/1999 |
| WO | WO0232325 A1 | 4/2002 |
| WO | WO03063946 A2 | 8/2003 |
| WO | WO03063953 A2 | 8/2003 |
| WO | WO03089045 A2 | 10/2003 |
| WO | WO2004073791 A1 | 9/2004 |
| WO | WO2005030322 A1 | 4/2005 |
| WO | WO2006105066 A2 | 3/2006 |
| WO | WO2006093685 A1 | 9/2006 |
| WO | WO2007047966 A2 | 4/2007 |
| WO | WO2007089986 A1 | 8/2007 |
| WO | WO2007118194 A2 | 10/2007 |
| WO | WO2008051122 A1 | 5/2008 |
| WO | WO2009137186 A1 | 11/2009 |
| WO | WO2010078552 A1 | 7/2010 |
| WO | 2011081713 A1 | 7/2011 |
| WO | 2012038378 A1 | 3/2012 |
| WO | 2014066010 A1 | 5/2014 |
| WO | 2015130753 A1 | 9/2015 |

OTHER PUBLICATIONS

"High Voltage Engineering and Testing, 2nd Edition", edited by Hugh M. Ryan, Institution of Engineering and Technology, 2001, 15 pages.

Avalanche Breakdown, Wikipedia Article, captured Apr. 6, 2010, [http://en.wikipedia.org/wiki/Avalanche_breakdown].

Basso, Christophe, "SPICE Model Simulates Spark-Gap Arrestor", Electronics Design, Strategy, and News (EDN), Jul. 3, 1997, 4 pages.

Citel Inc., Data Sheet, BH Series 2 Electrode Miniature Gas Discharge Tube Surge Arrester—8mm, May 14, 2009, 2 pages.

File History for U.S. Appl. No. 11/015,807, filed Dec. 17, 2004 to Cooke, Daniel J. et al.

Gray, Robert W. et al., "Simple design changes to wires to substantially reduce MRI-induced heating at 1.5 T: implications for implanted leads", Magnetic Resonance Imaging 23 (2005) 887-891.

Hayes, David L., Chapter 4, "Generator and Lead Selection" from book entitled "Cardiac Pacing and Defibrillation a Clinical Approach", John Wiley & Sons, (c) 2000 Mayo Foundation, p. 129-157.

International Preliminary Examination Report issued in PCT/US2013/065517, completed Apr. 21, 2015, 8 pages.

International Search Report and Written Opinion issued in PCT/US2008/085518 on Oct. 29, 2009, 15 pages.

International Search Report and Written Opinion issued in PCT/US2009/032838, mailed May 4, 2009, 14 pages.

International Search Report and Written Opinion issued in PCT/US2009/038629, mailed Jun. 29, 2009, 11 pages.

(56) References Cited

OTHER PUBLICATIONS

International Search Report and Written Opinion issued in PCT/US2009/056843, mailed Dec. 29, 2009, 13 pages.
International Search Report and Written Opinion issued in PCT/US2010/024062, mailed Sep. 27, 2010.
International Search Report and Written Opinion issued in PCT/US2010/033686 on Aug. 10, 2010, 12 pages.
International Search Report and Written Opinion issued in PCT/US2010/048620, mailed Apr. 5, 2011, 10 pages.
International Search Report and Written Opinion issued in PCT/US2010/053223, mailed Dec. 27, 2010, 11 pages.
International Search Report and Written Opinion issued in PCT/US2010/055130, mailed Mar. 10, 2011, 11 pages.
International Search Report and Written Opinion issued in PCT/US2010/055653, mailed Feb. 1, 2011, 14 pages.
International Search Report and Written Opinion issued in PCT/US2011/052541, dated Mar. 9, 2012, 22 pages.
International Search Report and Written Opinion issued in PCT/US2012/055673, mailed Dec. 13, 2012, 10 pages.
International Search Report and Written Opinion issued in PCT/US2013/037432, mailed Nov. 19, 2013, 17 pages.
International Search Report and Written Opinion issued in PCT/US2013/057732, mailed Dec. 13, 2013, 11 pages.
Invitation to Pay Additional Fees and Partial Search Report, dated Aug. 17, 2009, issued in PCT/US2008/085533, 6 pages.
Invitation to Pay Additional Fees and Partial Search Report, issued in PCT/US2010/024062, mailed May 7, 2010.
Partial International Search Report issued in PCT/US2011/052541, mailed Dec. 6, 2011, 4 pages.
Partial International Search Report issued in PCT/US2013/013432, mailed Jul. 17, 2013, 6 pages.
Partial International Search Report issued in PCT/US2013/037432, mailed Jul. 17, 2013, 6 pages.
Static Spark Gap Analysis, captured Dec. 24, 2002, [http://www.richieburnett.co.uk/static.html].
Third Party Submission Under 37 CFR 1.290 filed in U.S. Appl. No. 14/056,746 on May 20, 2014, 13 pages.
International Search Report and Written Opinion issued in PCT/US2015/017473, mailed May 20, 2015, 10 pages.
International Preliminary Report on Patentability issued in PCT/US2015/017473, mailed Sep. 9, 2016, 8 pages.

CONSTRUCTION OF AN MRI-SAFE TACHYCARDIA LEAD

CROSS-REFERENCE TO RELATED APPLICATION

This application claims priority to Provisional Application No. 61/945,081, filed Feb. 26, 2014, which is herein incorporated by reference in its entirety.

TECHNICAL FIELD

The present invention relates to implantable medical devices and methods of manufacturing. More specifically, the invention relates to MRI compatible medical device lead and methods for manufacturing MRI compatible medical device lead.

BACKGROUND

Various medical devices are commonly used to treat patients suffering from chronic and/or disabling diseases such as chronic pain, Parkinson's disease, cardiac arrhythmias. Few of these medical devices are temporarily or permanently implanted within patient's body. Such medical devices include neurostimulators, cardiac pacemakers, or implantable cardioverter-defibrillators (ICDs) (collectively Implantable Medical Devices (IMDs)).

Generally, an IMD includes an implantable pulse generator and one or more conducting leads with electrodes used to conduct signals between the heart and the implantable pulse generator (IPG). Commonly, the IMD is implanted into the pectoral region of the patient's body. The leads extend from the IPG to stimulate one or more chambers of the heart. The leads are used to deliver therapy to the patient and each include one or more conducting cables, electrodes, and/or coils.

Further, in some scenarios, the patient with an IMD may need to undergo a Magnetic Resonance Imaging (MRI) scan. An MRI is a non-invasive imaging modality that utilizes a magnetic field and radio frequency (RF) pulses to generate images of various anatomical structures within a patient's body. Typically, an MRI scanner uses a magnet to create a strong static magnetic field to align the protons of hydrogen atoms in the patient's body. Then, the patient is exposed to RF pulses of electromagnetic energy causing the protons to spin about their axis. Once the RF pulses are removed, these protons tend to come back to their resting state aligned with the static magnetic field. The MRI scanner detects the signal generated by the spinning protons that is processed to create an image.

During the MRI scan, the RF pulses may be picked up by leads implanted within a patient's body. There is a need for improved lead design to minimize induced currents generated from MRI energy.

SUMMARY

In Example 1, a medical device lead, comprising a lead body, an electrical conductor and a tubular conductive element. The lead body includes a tubular member having a proximal end, a distal end, and a conductor lumen extending therebetween, wherein the tubular member is made of an electrically insulative material. The electrical conductor extends within the conductor lumen from the proximal end of the tubular member toward the distal end of the tubular member. The tubular conductive element is disposed over the tubular member of the lead body between the proximal and distal ends thereof. The tubular conductive element has one or more kerfs formed therethrough so as to affect an electrical property thereof, and wherein the electrical conductor is electrically coupled to the tubular conductive element.

In Example 2, the medical device lead of Example 1, wherein the one or more kerfs are formed in a helical pattern such that electrical current passing through the tubular conductive element travels along a helical path.

In Example 3, the medical device lead of either of Examples 1 or 2, wherein the one or more kerfs have a constant pitch.

In Example 4, the medical device lead of either of Examples 1 or 2, wherein the one or more kerfs have a variable pitch.

In Example 5, the medical device lead of any of Examples 1-4, wherein the first segment defines an electrode of the medical device lead.

In Example 6, the medical device lead of any of Examples 1-5, wherein the tubular conductive element includes a first segment and a second segment extending distally from the first segment, wherein the one or more kerfs are formed in each of the first and second segments so as to affect an electrical property of the first and second segments, wherein the first segment has a higher electrical impedance than the second segment.

In Example 7, the medical device lead of Example 6, further comprising a layer of insulative material disposed over the first segment.

In Example 8. the medical device lead of either of Examples 6 or 7, wherein the first segment is operable to inhibit induced currents in the tubular conductive element in the presence of an external source of electromagnetic energy.

In Example 9, the medical device lead of any of Examples 1-5, wherein the tubular conductive element includes first, second and third segments, the second segment extending distally from the first segment, and the third segment extending distally from the second segment, wherein the one or more kerfs are formed in each of the first, second and third segments, and wherein the one or more kerfs in each of the first and second segments are configured so that the first and second segments have a higher electrical impedance than the third segment.

In Example 10, the medical device lead of Example 9, further comprising a layer of insulative material disposed over the first and second segments of the tubular conductive element, so that the first and second segments of the tubular conductive element are operable to inhibit induced currents in the tubular conductive element in the presence of an external source of electromagnetic energy.

In Example 11, the medical device lead of Example 10, wherein an outer surface of the third segment of the tubular conductive element is uninsulated so that the third segment can be operable as a shocking electrode.

In Example 12, the medical device lead of any of Examples 9-11, wherein the electrical conductor is mechanically and electrically coupled to the tubular conductive element at a connection location disposed at a transition between the first and second segments of the tubular conductive element.

In Example 13, the medical device lead of any of Examples 9-11, wherein the first, second and third segments are formed from a single tube of conductive material.

In Example 14, the medical device lead of any of Examples 9-11, wherein one or more of the first, second and third segments are formed from separate tubes of conductive material and subsequently joined together by a weld joint.

In Example 15, the medical device lead of any of Examples 9-14, wherein the kerfs in the third segment include a series of kerfs each extending partially circumferentially about the tubular conductive element and distributed along the length of the third segment, wherein each kerf in the third segment is circumferentially offset from adjacent kerfs so as to cause electrical current to assume a non-linear flow path through the third segment.

In Example 16, a medical device lead, comprising a lead body, an electrical conductor and a tubular conductive element. The lead body includes a tubular member having a proximal end and a distal end and a conductor lumen extending therebetween, wherein the tubular member is made of an electrically insulative material. The electrical conductor extends within the conductor lumen from the proximal end of the tubular member toward the distal end of the tubular member. The tubular conductive element is disposed over the tubular member of the lead body between the proximal and distal ends thereof. The tubular conductive element includes a first segment, a second segment extending distally from the first segment, and a third segment extending distally from the second segment, each of the segments having one or more kerfs formed radially therethrough in a predetermined configuration so as to affect an electrical impedance of the respective segment. The one or more kerfs in each of the first and second segments are configured so that the first and second segments have a higher electrical impedance than the third segment, and the electrical conductor is mechanically and electrically coupled to the tubular conductive element. A layer of insulative material is disposed over the first and second segments of the tubular conductive element. The first and second segments of the tubular conductive element are operable to inhibit induced currents in the tubular conductive element in the presence of an external source of electromagnetic energy. An outer surface of the third segment of the tubular conductive element is uninsulated so that the third segment can be operable as a shocking electrode.

In Example 17, the medical device lead of Example 16, wherein the electrical conductor is mechanically and electrically coupled to the tubular conductive element at a connection location disposed at a transition between the first and second segments of the tubular conductive element.

In Example 18, the medical device lead of either of Examples 16 or 17, wherein the kerfs in the first and second segments are formed in a helical pattern along a length thereof.

In Example 19, the medical device lead of any of Examples 16-18, wherein the kerfs in the first segment have a constant pitch along the length of the first segment.

In Example 20, the medical device lead of any of Examples 16-19, wherein the kerfs in the second segment have a constant pitch along the length of the second segment.

In Example 21, the medical device lead of any of Examples 16-18, wherein the kerfs in one or both of the first and second segments have a pitch that varies along the length of the respective segment.

In Example 22, the medical device lead of Example 21, wherein the pitch of the kerfs in one or both of the first and second segments decrease with distance from the connection location.

In Example 23, the medical device lead of any of Examples 16-22, wherein the kerfs in the third segment include a series of kerfs each extending partially circumferentially about the tubular conductive element and distributed along the length of the third segment, wherein each kerf in the third segment is circumferentially offset from adjacent kerfs so as to cause electrical current to assume a non-linear flow path through the third segment.

In Example 24, the medical device lead of any of Examples 16-23, wherein the first, second and third segments are formed from a single tube of conductive material.

In Example 25, the medical device lead of any of Examples 16-23, wherein one or more of the first, second and third segments are formed from separate tubes of conductive material and subsequently joined together by a weld joint.

In Example 26, a filtered electrode component for an implantable medical device lead, the filtered electrode component comprising a tubular conductive element including a first segment, a second segment extending distally from the first segment, and a third segment extending distally from the second segment, each of the segments having one or more kerfs formed radially therethrough in a predetermined configuration so as to affect an electrical impedance of the respective segment. The one or more kerfs in each of the first and second segments are configured so that the first and second segments have a higher electrical impedance than the third segment, and the tubular conductive element is configured to be mechanically and electrically coupled to an electrical conductor.

In Example 27, the filtered electrode component of Example 26, wherein the kerfs in the first and second segments are formed in a helical pattern along a length thereof.

In Example 28, the filtered electrode component of either of Examples 26 or 27, wherein the kerfs in one or both of the first and second segments has a constant pitch along the length of the respective segment.

In Example 29, the filtered electrode component of either of Examples 27 or 28, wherein the kerfs in one or both of the first and second segments have a pitch that varies along the length of the respective segment.

In Example 30, the filtered electrode component of Example 29, wherein the pitch of the kerfs in one or both of the first and second segments decreases with distance from the other of the first and second segments.

In Example 31, the filtered electrode component of any of Examples 26-30, wherein the kerfs in the third segment include a series of kerfs each extending partially circumferentially about the tubular conductive element and distributed along the length of the third segment, wherein each kerf in the third segment is circumferentially offset from adjacent kerfs so as to cause electrical current to assume a non-linear flow path through the third segment.

In Example 32, a method of forming an electrical component for a medical device lead, comprising mounting a tubular conductive element to a fixture, and cutting one or more kerfs radially through the tubular conductive element using a laser in one or more predetermined patterns configured so as to affect an electrical property of the tubular conductive element.

In Example 33, the method of Example 32, wherein cutting one or more kerfs includes cutting a first pattern of kerfs in a helical path along a first length of the tubular conductive element, and cutting a second pattern of kerfs in a non-helical pattern along a second length of the tubular conductive element.

In Example 34, the method of either of Examples 32 or 33, wherein cutting one or more kerfs includes cutting first, second and third patterns of kerfs to define first, second and third segments of the tubular conductive element, wherein the first and second patterns are helical patterns each having a variable pitch that decreases with distance from the other of the first and second patterns, and wherein the third pattern is a non-helical pattern, so that the first and second segments have an electrical impedance that is higher than an electrical impedance of the third segment.

In Example 35, the method of any of Examples 32-34, wherein the tubular conductive element is a first tubular conductive element, and wherein the method further comprises cutting one or more kerfs radially through a second tubular conductive element using a laser in one or more predetermined patterns configured so as to affect an electrical impedance of the second tubular conductive element, and mechanically and electrically joining the first and second tubular conductive elements.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
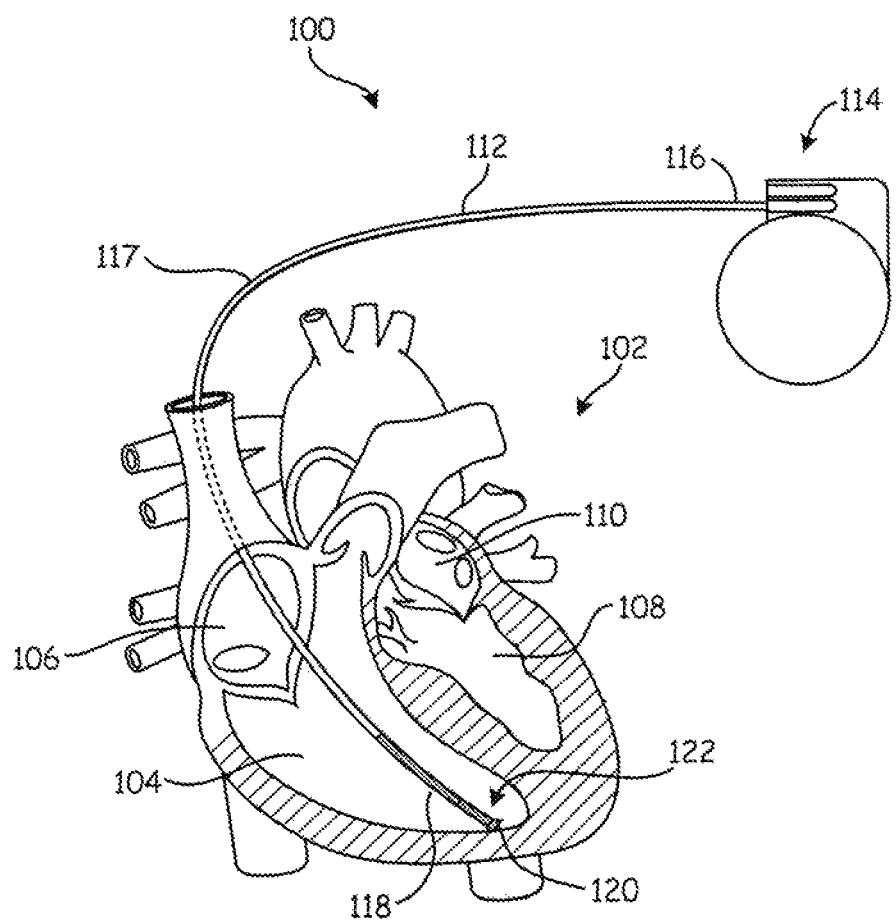
FIG. 1 is a schematic illustration of a cardiac rhythm management (CRM) system including a defibrillation lead and a pulse generator according to one embodiment.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic illustration of a cardiac rhythm management (CRM) system 100 providing therapy to a patient's heart 102, which includes a right ventricle 104, right atrium 106, left ventricle 108, and left atrium 110. The CRM system 100 includes a medical device lead 112 such as a defibrillation lead and a pulse generator 114 coupled to a proximal end 116 of the lead 112 to perform desired set of operations. The pulse generator 114 generates signals for delivering treatment to the heart 102 with pacing and/or defibrillation capabilities. In various embodiments, the pulse generator 114 is an implantable cardioverter-defibrillator (ICD). In some embodiments, the CRM system 100 may include multiple leads for delivering therapy.

In some embodiments, the lead 112 includes a lead body 117, a shocking electrode 118, a pacing/sensing electrode 120, and one or more conductors (not shown in FIG. 1). The shocking electrode 118 is disposed proximate a distal end 122 of the lead 112 and is coupled to at least one conductor and is configured to deliver shock to the patient's heart 102 in scenarios when an anomaly, such as an arrhythmia, is sensed or detected. The electrode 120 is disposed at the distal end 122 of the lead 112 and is also connected to at least one conductor that enables the electrode 120 to sense and pace the patient's heart 102. The conductor enables the electrode 120 to sense and pace by conducting electrical signals generated by the heart 102 to the pulse generator 114 and the electrical pulses generated by the pulse generator 114 for pacing to the heart 102.

In the illustrated embodiment, the lead 112 is deployed in the right ventricle 104. However, in other embodiments, the lead 112 can be implanted in the right atrium 106 or both the right atrium 106 and the right ventricle 104, or a left chamber of the heart 102. In various embodiments, two or more leads 112 may be deployed within the heart 102 at different target regions.

The pulse generator 114 generally includes a power source and electronic circuitry configured to process and generate electrical signals. The power source includes a battery that provides power to the CRM system 100 to perform its operations. The electronic circuitry may include components for memory, processing, or the like. In some embodiments, the pulse generator 114 is implanted by forming a subcutaneous pocket in the pectoral girdle of the patient. Optionally, the pulse generator 114 can also be implanted in the thoracic cavity, abdominal region, neck region, or the like.

The following embodiments are primarily described in context of the CRM system 100. However, the skilled artisan will readily understand that the embodiments may also be used in conjunction with other implantable medical devices such as, but not limited to, deep brain stimulators, spinal cord stimulators, or the like.

Figure 2:
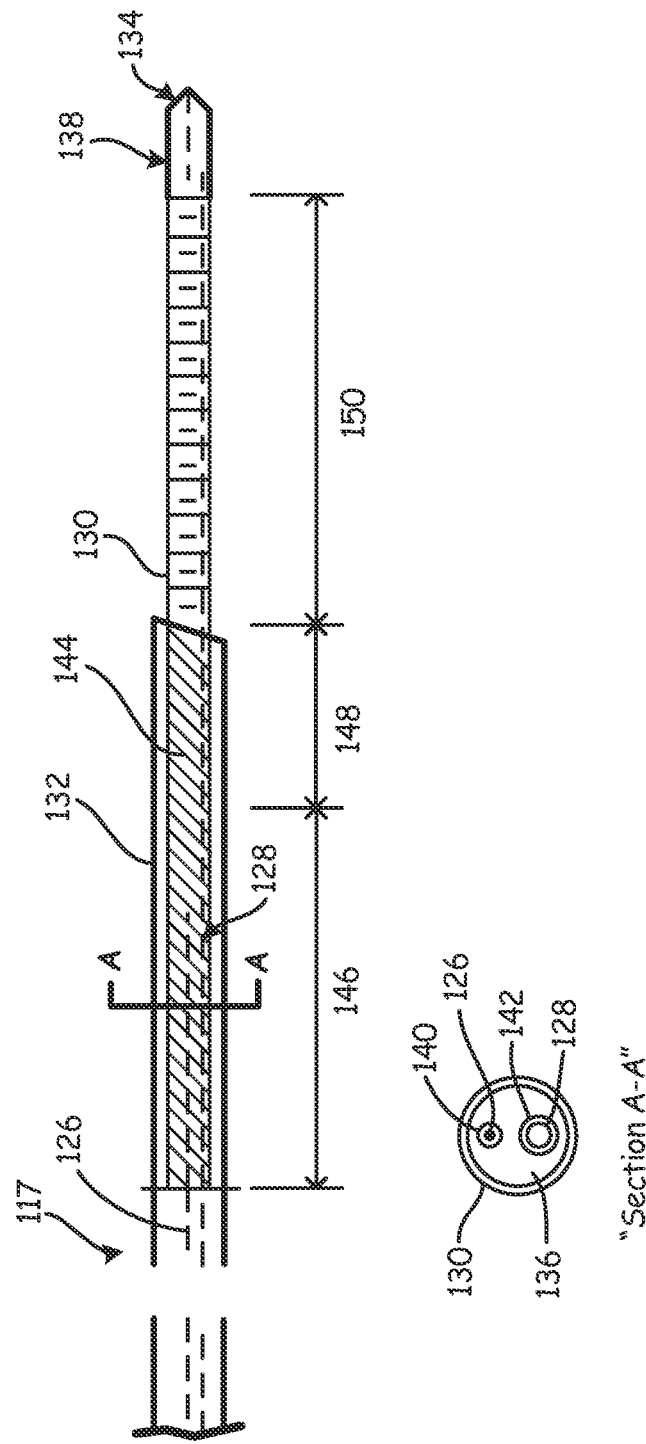
FIG. 2 is a schematic illustration of the defibrillation lead illustrated in FIG. 1 according to one embodiment.

FIG. 2 is a schematic illustration of the lead 112 illustrated in FIG. 1, according to one embodiment. The lead 112 includes the lead body 117, an electrical conductor 126, a low voltage conductor 128, a tubular conductive element 130, a layer of insulative material 132, and a tip electrode 134. In some embodiments, the tubular conductive element 130 is disposed over the lead body 117 that encompasses the electrical conductor 126 and the low voltage conductor 128 as shown in Section A-A of FIG. 2.

More particularly, the lead body 117 includes an insulative tubular member 136 having a proximal end (not shown in FIG. 2), a distal end 138, one or more conductor lumens (shown in Section A-A) extending either partially or entirely between the proximal end and the distal end 138 of the tubular member 136. In the illustrated embodiment, the tubular member 136 defines a first conductor lumen 140 that has a profile slightly smaller than that of a second conductor lumen 142.

The first conductor lumen 140 is configured to receive the electrical conductor 126. In some embodiments, the electrical conductor 126 can be a high voltage cable or wire extending from the proximal end of the tubular member 136 towards the distal end 138. The electrical conductor 126 is configured to carry high voltage electrical signals from the pulse generator 114 to deliver shock to the heart 102 (see FIG. 1). To deliver shocks, the electrical conductor 126 is electrically coupled to the tubular conductive element 130 at a connection location 144.

In some embodiments, the tubular conductive element 130 is a tube like structure including a proximal segment 146, an intermediate segment 148, and a distal segment 150. In various embodiments, the proximal segment 146 and the intermediate segment 148 are operable to filter electromagnetic energy from an external source such as an MRI. The distal segment 150 is operable as a shocking electrode configured to deliver shock to the heart 102. The layer of insulative material 132 is disposed over the proximal segment 146 and the intermediate segment 148 such that these segments will not be able to deliver energy to surrounding tissue.

In various embodiments, the lead 112 may include two or more tubular conductive elements 130 disposed along its length, a distal tubular conductive element, and a proximal tubular conductive element. In an example, the distally located tubular conductive element is positioned within the right ventricle 104 and the proximally located tubular conductive element is positioned within the right atrium 106 or superior vena cava. The two tubular conductive elements may be independently activated based on the requirement of therapy.

The second conductor lumen 142 is configured to receive a conductor such as a low voltage conductor 128. In some embodiments, the low voltage conductor 128 extends to the tip electrode 134 at the distal end 138 of the insulative tubular member 136 of the lead body 117. In one embodiment, the low voltage conductor 128 can be in the form of a single- or multi-filar coil conductor. In various embodiments, the low voltage conductor 128 can be a non-coiled conductor (e.g., a multi-strand cable, or the like). The low voltage conductor 128 is configured to convey electrical signals from the heart 102, such as electrical activity of the heart 102, to the pulse generator 114 to detect abnormal rhythms. The low voltage conductor 128 may also transmit pacing signals from the pulse generator 114 to the heart 102. In various embodiments, the low voltage conductor 128 can be configured as a relatively high inductance coil to inhibit induced currents in the conductor. In some embodiments, the low voltage conductor 128 may define a lumen configured to receive a stylet or guide wire (not shown) for implanting the lead 112 within the patient's body.

The tip electrode 134 connected to the distal end of the low voltage conductor 128 is in contact with the tissue, such as heart tissue, for sensing electrical signals produced by the heart 102 and/or pacing the heart 102 by transmitting the pulses generated by the pulse generator 114. In some embodiments, the tip electrode 134 can be engaged with the tissue by active fixation such as a helix screw that can be inserted into the tissue by rotation of the helix screw. To accomplish rotation of the helix screw, the tip electrode 134 is mechanically coupled to the low voltage conductor 128, which in turn is mechanically coupled to a rotatable element (e.g., a terminal pin) at the proximal end of the lead. In such scenarios, the tip electrode 134 conducts as well as secures, the lead 112 to the cardiac tissue. In other embodiments, the tip electrode 134 can be passively engaged with the tissue just by contacting the tissue, such as a ring electrode, a ball shape electrode, or the like.

In some embodiments, the layer of insulative material 132 and the insulative tubular member 136 can be formed using a suitable electrically insulative biocompatible material such as, but not limited to, silicone, polytetrafluoroethylene (PTFE), ethylene tetrafluoroethylene (ETFE), fluorinated ethylene propylene (FEP), polyvinylchloride (PVC), polyether-ester, polyamide, polyetheretherketone (PEEK), or the like. In some embodiments, the tubular member 136 and the conductor lumens 140, 142 have a circular cross-section. However, other suitable cross-sectional shapes may also be contemplated, such as but not limited to, rectangular, square, triangular, oval, or the like.

Figure 3:
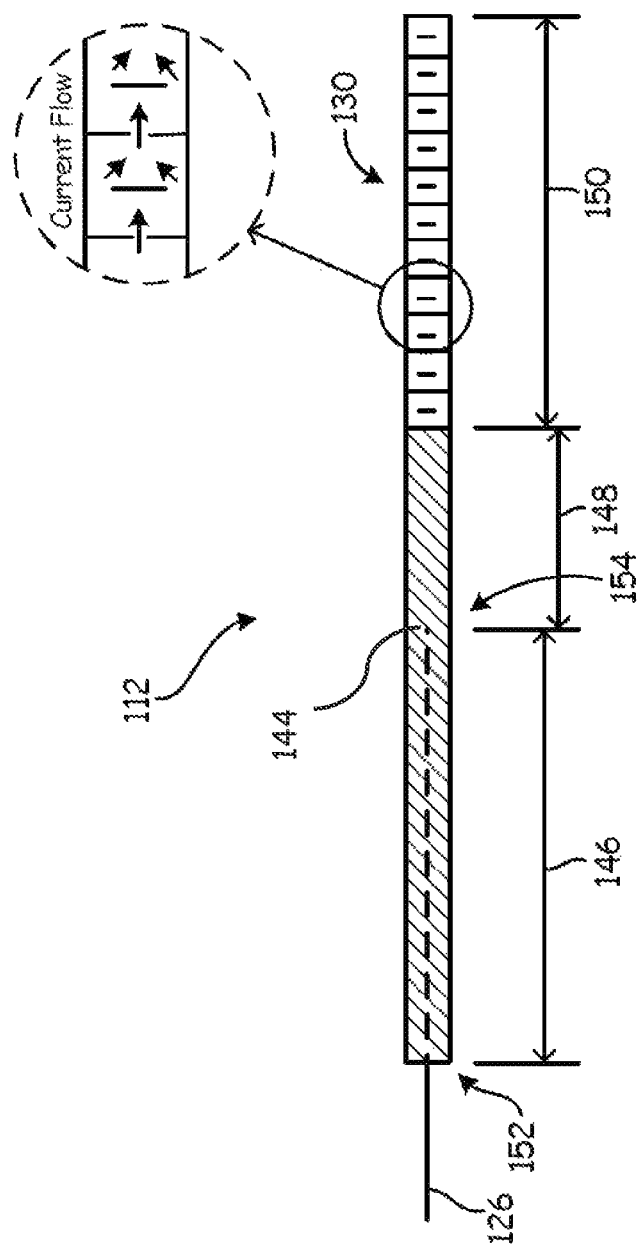
FIGS. 3-5 are schematic illustrations of shocking electrode and MRI filter arrangements for the defibrillation lead of FIG. 1 according to various embodiments.

FIG. 3 is a schematic illustration of a shocking electrode (such as shocking electrode 118 of FIG. 1) and MRI filter arrangement for the lead 112 of FIG. 1. The shocking electrode and MRI filter arrangement together forms a part of the tubular conductive element 130. As shown, the tubular conductive element 130 includes the proximal segment 146, the intermediate segment 148 extending distally from the proximal segment 146, and the distal segment 150 extending distally from the intermediate segment 148. The proximal, intermediate, and distal segments 146, 148, 150, respectively, each include patterns of kerfs formed radially through the wall defining the tubular conductive element 130. The kerfs are slots created by cutting (e.g., laser cutting) or otherwise removing (e.g., by etching) material of the tubular conductive material 130 in a predetermined pattern. In some embodiments, the proximal segment 146, and the intermediate segment 148 constitutes the MRI filter arrangement and the distal segment 150 is the shocking electrode.

The proximal segment 146 includes a proximal end 152, a distal end 154, and a coiled conductor extending between the proximal end 152 and the distal end 154.

Referring to FIGS. 2 and 3, in some embodiments, the proximal segment 146 is operable as a transmission line filter configured to shield the electrical conductor from RF energy produced during an MRI scan, so as to cancel the effect of MRI interference in the electrical conductor 126. The electrical conductor 126 is connected to the tubular conductive element 130 between the proximal segment 146 and the intermediate segment 148 at the connection location 144. As shown, the distal end 154 of the proximal segment 146 is coupled to the electrical conductor 126.

The intermediate segment 148 is operable as an in-line tuning filter used to tune or choke the RF signals induced due to RF pulsating magnetic field or the MRI environment. The intermediate segment 148 has an inductance that poses high impedance to certain frequencies without affecting the flow of electrical signals generated by the pulse generator (such as pulse generator 114). When an alternating current is induced in the lead 112 due to RF signals, a magnetic field is generated around the intermediate segment 148 and this field opposes any further current changes. This enables the intermediate segment 148 to attenuate the undesired current or voltage signals generated within the lead 112 or the electrical conductor 126 such that the signals generated are not transmitted to other parts of the lead 112, particularly the shocking electrode. In some embodiments, the proximal segment 146 and the intermediate segment 148 may be tuned to different MRI frequencies such as 64 MHz, 128 MHz or other frequencies involved during MRI procedure.

In some embodiments, the proximal segment 146 and the intermediate segment 148 are configured and arranged to have kerfs formed in a helical pattern around the circumference and length of the tubular conductive element 130, such that the remaining conductive material also extends in a helical configuration. In various embodiments, the pitch (i.e., the distance between adjacent turns of the helically-arranged kerfs) can be substantially uniform along the length of the proximal and/or intermediate segments 146, 148. Alternatively, one or both of the proximal and distal segments 146, 150 can be configured such that the pitch(es) of the kerfs varies along all or part of the length of the segment. The variable pitch may alter the electrical properties of the proximal segment 146 and/or the intermediate segment 148. In one embodiment, the proximal segment 146 and the intermediate segment 148 are configured so as to have smaller pitch near the connection location 144.

The distal segment 150 forms a distal portion of the tubular conductive element 130. The distal segment 150 is operable as the shocking electrode configured to deliver shock or high voltage pulses to the heart. In the illustrated embodiment, the distal segment 150 is designed to have kerfs extending partially along the circumference of the tubular conductive element 130. When the electrical signal is sent to the distal segment 150, the kerfs direct the current to take a non-linear path distributing energy over a larger surface area, and thereby minimizing heating of surrounding tissue.

In various embodiments, the tubular conductive element 130 can be formed using a suitable non-ferromagnetic conducting biocompatible material such as, but not limited to, Nitinol™, gold, silver, stainless steel, copper, platinum, or a combination of these materials.

Figure 4:
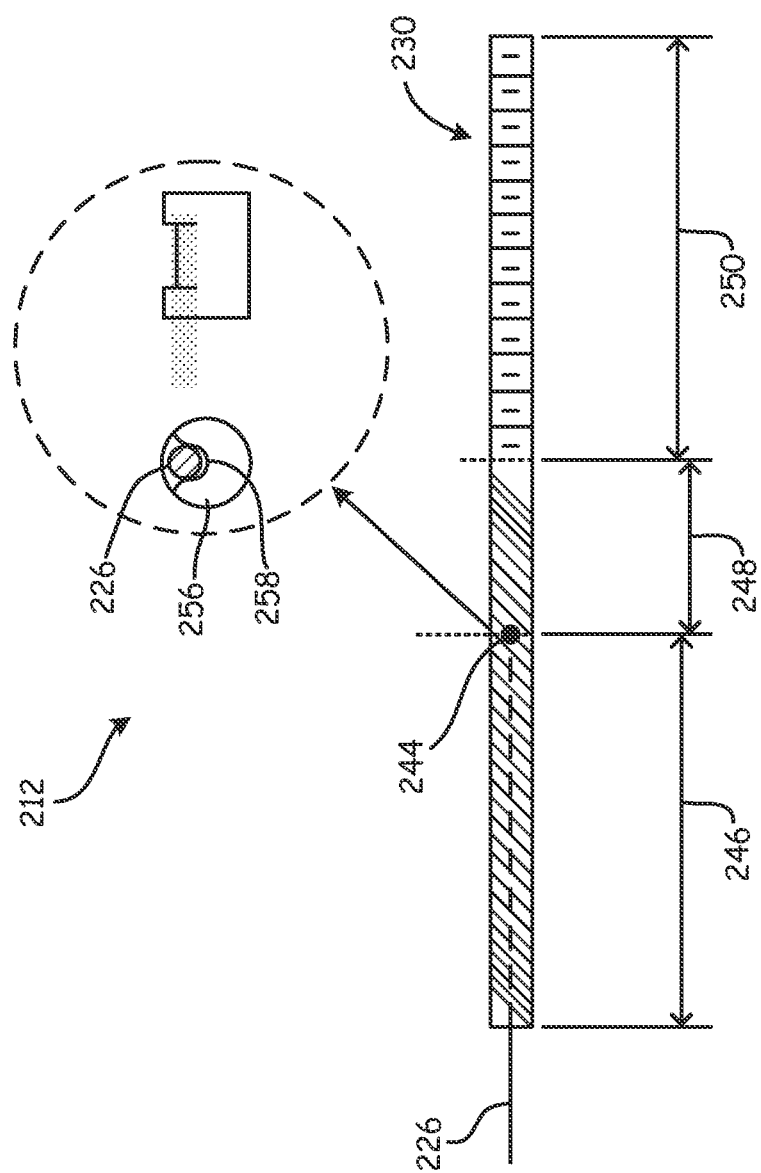

FIG. 4 is a schematic illustration of a shocking electrode and MRI filter arrangement for a lead 212 similar to lead 112 of FIG. 1 manufactured from a single tube of conductive material. In the illustrated embodiment, a tubular conductive element 230 includes a proximal segment 246, an intermediate segment 248, and a distal segment 250 formed by forming kerfs through the wall of a unitary tube. The electrical conductor 226 is mechanically and electrically coupled to the tubular conductive element 230 at a connection location 244 between the proximal segment 246 and the intermediate segment 248.

In some embodiments, a connector 256 (as shown in the detail view of FIG. 4) is used to couple the electrical conductor 226 to the tubular conductive element 230. In the illustrated embodiments, the connector 256 includes a saddle-shaped portion 258 configured to receive a distal end of the electrical conductor 226. The electrical conductor 226 is placed within the saddle-shaped portion 258 of the connector 256 and coupled to the connector 256. For fixation, techniques such as welding, soldering, heat bonding, crimping, or the like may be used. In some embodiments, the connector 256 includes a flap configured to tightly secure the electrical conductor 226 with the connector 256. Upon fixation, the connector 256, along with the electrical conductor 226, is disposed within the tubular conductive element 230. Then, the connector 256 is coupled to the tubular conductive element 230 by a suitable technique such as, but not limited to, welding, soldering, or the like. In some embodiments, the connector 256 is a metallic ring that electrically couples the electrical conductor 226 to the tubular conductive element 230.

Additionally, as shown, the proximal segment 246 and the intermediate segment 248 have variable pitches. In some embodiments, the pitches of the kerfs in the proximal segment 246 and the intermediate segment 248 decrease in a direction away from the connection location 244 where the electrical conductor 226 is coupled to the tubular conductive element 230 to reduce reflection at the connection location 244.

Figure 5:
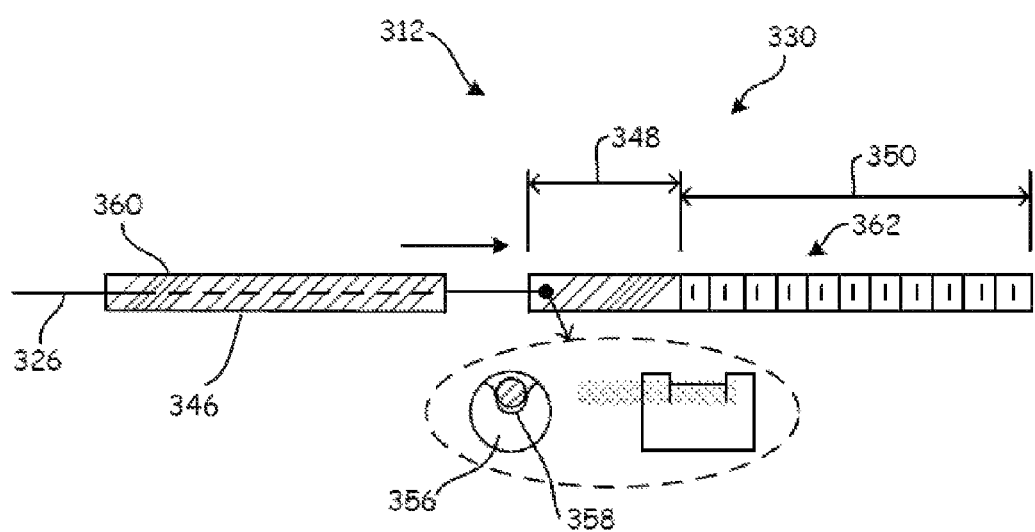

FIG. 5 is a schematic illustration of a shocking electrode and MRI filter arrangement for a lead 312, similar to the lead 112 of FIG. 1, manufactured from two tubes of conductive material. The shocking electrode and the MRI filter arrangement can be configured substantially similar to the shocking electrode and MRI filter arrangement of FIG. 4 except as described below. In the illustrated embodiment, the tubular conductive element 330 is formed by joining a first tube 360 and a second tube 362 at a weld joint. The first tube 360 includes a proximal segment 346 and the second tube 362 includes an intermediate segment 348 and a distal segment 350. A connector 356 having a saddle-shaped portion 358, similar to the connector 256 of FIG. 4, is coupled to an electrical conductor 326 and the second tube 362. Then, the first tube 360 is slid over the electrical conductor 326 and coupled to the second tube 362 forming the tubular conductive element 330. Coupling of the first tube 360 to the second tube 362 can be achieved by any suitable technique known in the art. Exemplary techniques include welding, soldering, heat bonding, or the like.

Figure 6:
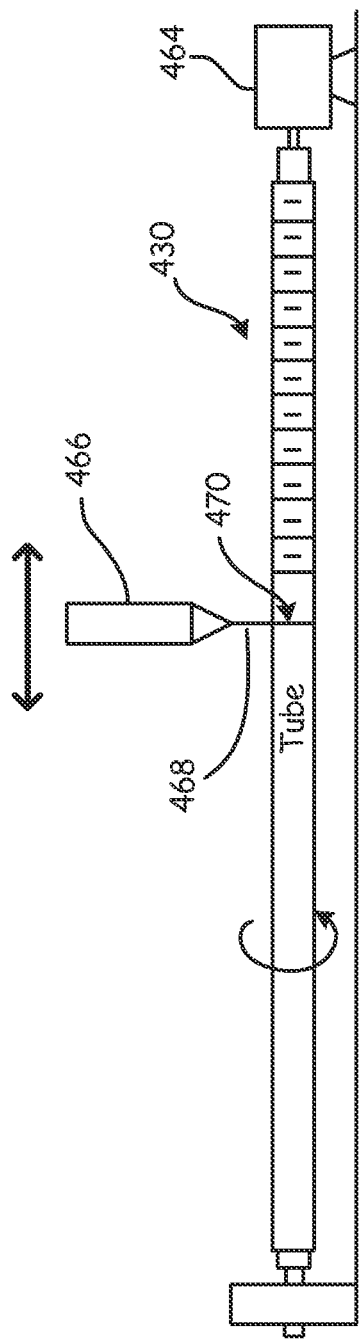
FIG. 6 is a schematic illustration showing a technique for manufacturing a shocking electrode and MRI filter arrangement for the defibrillation lead of FIG. 1 according to various embodiments.

FIG. 6 is a schematic illustration showing a technique for manufacturing a shocking electrode and MRI filter arrangement for the lead of FIG. 1 according to various embodiments. In the illustrated embodiment, the shocking electrode and the MRI filter arrangement can be from a single tube of conductive material. The tubular conductive element 430 is mounted on a fixture 464. The fixture 464 is configured to hold and rotate the tubular conductive element 430 in a predefined manner. The fixture 464 may engage with a distal and/or a proximal end of the tubular conductive element 464.

Further, a laser 466 is deployed at a position over the tubular conductive element 430 mounted on the fixture 464. The laser 466 is configured to generate a high intensity light beam 468 and move axially in a transverse plane for cutting one or more kerfs 470 radially through the tubular conductive element 430. The laser 466 emits a high intensity beam of light that is made to fall on the tubular conductive element 430. The energy of the light beam 468 is transferred to the tubular conductive element 430, thereby melting and/or vaporizing the material of the tubular conductive element 430 and forming the kerfs 470. In some embodiments, the motion of the laser 466 can be controlled by an automated system causes the laser 466 output to follow a predetermined pattern.

In various embodiments, a $CO_2$ laser is used to form the kerfs 470. Other suitable examples of the laser 466 that can be used to from the kerfs 470 include, but are not limited to, Nd-YAG laser, YAG laser, or the like. Alternatively, in some embodiments, plasma techniques may be employed to form kerfs 470 through the tubular conductive element 430.

In the various embodiments, the kerfs 470 can be formed so as to affect the electrical properties of the tubular conductive element 430. In some embodiments, a first pattern (not shown) of the kerfs 470 is cut along a first length of the tubular conductive material 430 and a second pattern of the kerfs 470 is cut along a second length of the tubular conductive element 430. The first pattern of the kerfs 470 includes a helical path formed along the first length, including the proximal segment and the intermediate segment. Further, in the illustrated embodiment, the second pattern of the kerfs 470 can include a helical pattern or a non-helical pattern along the second length. As shown, the non-helical pattern includes cuts or slots formed that extend partially along the circumference of the tubular conductive element 430.

In other embodiments, the kerfs 470 include a first pattern, a second pattern, and a third pattern of kerfs defined along different portions of the tubular conductive element 430. The first pattern defines a proximal segment (similar to proximal segment 146), a second pattern defines an intermediate segment (similar to intermediate segment 148), and a third pattern defines a distal segment (similar to distal segment 150) of the tubular conductive element 430. In a preferred embodiment, the first and the second patterns are helical patterns having a variable pitch. The variable pitch decreases with distance from the other of the first and second patterns. The third pattern is a non-helical pattern such that the proximal and intermediate segments have electrical impedances higher than the electrical impedance of the distal segment.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A medical device lead, comprising:
a lead body including a tubular member having a proximal end, a distal end, and a conductor lumen extending therebetween, the tubular member made of an electrically insulative material;
an electrical conductor extending within the conductor lumen from the proximal end of the tubular member toward the distal end of the tubular member;
a tubular conductive element disposed over the tubular member of the lead body between the proximal and distal ends thereof, the tubular conductive element including a first segment, a second segment extending distally from the first segment, and a third segment extending distally from the second segment, each of the segments having one or more kerfs formed radially therethrough in a predetermined configuration so as to affect an electrical impedance of the respective segment, wherein the one or more kerfs in each of the first and second segments are configured so that the first and second segments have a higher electrical impedance than the third segment, so that the first and second segments of the tubular conductive element are operable to inhibit induced currents in the tubular conductive element in the presence of an external source of electromagnetic energy, and wherein the electrical conductor is mechanically and electrically coupled to the tubular conductive element; and
a layer of insulative material disposed over the first and second segments of the tubular conductive element,
wherein an outer surface of the third segment of the tubular conductive element is uninsulated so that the third segment can be operable as a shocking electrode.

2. The medical device lead of claim 1, wherein the electrical conductor is mechanically and electrically coupled to the tubular conductive element at a connection location disposed at a transition between the first and second segments of the tubular conductive element.

3. The medical device lead of claim 2, wherein the kerfs in the first and second segments are formed in a helical pattern along a length thereof.

4. The medical device lead of claim 3, wherein the kerfs in the first segment have a constant pitch along the length of the first segment.

5. The medical device lead of claim 3, wherein the kerfs in the second segment have a constant pitch along the length of the second segment.

6. The medical device lead of claim 3, wherein the kerfs in one or both of the first and second segments have a pitch that varies along the length of the respective segment.

7. The medical device lead of claim 6, wherein the pitch of the kerfs in one or both of the first and second segments decrease with distance from the connection location.

8. The medical device lead of claim 1, wherein the kerfs in the third segment include a series of kerfs each extending partially circumferentially about the tubular conductive element and distributed along the length of the third segment, wherein each kerf in the third segment is circumferentially offset from adjacent kerfs so as to cause electrical current to assume a non-linear flow path through the third segment.

9. The medical device lead of claim 1, wherein the first, second, and third segments are formed from a single tube of conductive material.

10. The medical device lead of claim 1, wherein one or more of the first, second and third segments are formed from separate tubes of conductive material and subsequently joined together by a weld joint.

11. A filtered electrode component for an implantable medical device lead, the filtered electrode component comprising a tubular conductive element including a first segment, a second segment extending distally from the first segment, and a third segment extending distally from the second segment, each of the segments having one or more kerfs formed radially therethrough in a predetermined configuration so as to affect an electrical impedance of the respective segment, wherein the one or more kerfs in each of the first and second segments are configured so that the first and second segments have a higher electrical impedance than the third segment, and wherein the tubular conductive element is configured to be mechanically and electrically coupled to an electrical conductor.

12. The filtered electrode component of claim 11, wherein the kerfs in the first and second segments are formed in a helical pattern along a length thereof.

13. The filtered electrode component of claim 12, wherein the kerfs in one or both of the first and second segments has a constant pitch along the length of the respective segment.

14. The filtered electrode component of claim 12, wherein the kerfs in one or both of the first and second segments have a pitch that varies along the length of the respective segment.

15. The filtered electrode component of claim 14, wherein the pitch of the kerfs in one or both of the first and second segments decreases with distance from the other of the first and second segments.

16. The filtered electrode component of claim 11, wherein the kerfs in the third segment include a series of kerfs each extending partially circumferentially about the tubular conductive element and distributed along the length of the third segment, wherein each kerf in the third segment is circumferentially offset from adjacent kerfs so as to cause electrical current to assume a non-linear flow path through the third segment.

* * * * *